(12) United States Patent
Blau et al.

(10) Patent No.: US 6,176,241 B1
(45) Date of Patent: Jan. 23, 2001

(54) SYSTEM AND METHOD FOR CARDIORESPIRATORY CONDITIONING

(76) Inventors: Saul Blau, 31771 E. Nine Dr., Laguna Niguel, CA (US) 92677; Thomas W. Storer, 1041 Ave. B, Redondo Beach, CA (US) 90277; Christopher B. Cooper, 2260 Pelham Ave., Los Angeles, CA (US) 90064

( * ) Notice: Under 35 U.S.C. 154(b), the term of this patent shall be extended for 0 days.

(21) Appl. No.: 09/205,913

(22) Filed: Dec. 4, 1998

(51) Int. Cl.$^7$ ........................................... A61B 19/00
(52) U.S. Cl. ................................. 128/898; 600/300
(58) Field of Search ............................. 128/898, 719, 128/707, 671; 600/300

(56) References Cited

U.S. PATENT DOCUMENTS

| | | | |
|---|---|---|---|
| 4,463,764 | * | 8/1984 | Anderson et al. ............ 128/719 |
| 4,930,519 | * | 6/1990 | Anderson et al. ............ 128/671 |
| 5,297,558 | * | 3/1994 | Acorn et al. ................. 128/719 |
| 5,410,472 | * | 4/1995 | Anderson ..................... 364/413.04 |
| 5,598,849 | * | 2/1997 | Browne ........................ 128/707 |

* cited by examiner

*Primary Examiner*—Max Hindenburg
*Assistant Examiner*—Brian Szmal
(74) *Attorney, Agent, or Firm*—Stetina Brunda Garred & Brucker (57) ABSTRACT

Systems and methods for assessing cardiorespiratory fitness and for developing and implementing customized exercise regimens for developing cardiorespiratory conditioning. Initially, data is obtained from an individual to determine the individual's Anaerobic Threshold, Respiratory Compensation Point and $VO_2$max. Preferably, the individual's Anaerobic Threshold is determined by gas exchange analysis which compares either ventilatory equivalent ($V_E/VO_2$) versus oxygen uptake or $CO_2$ output versus oxygen uptake. Once the Anaerobic Threshold, Respiratory Compensation Point and $VO_2$max have been determined, exercise regimens can be formulated that are comprised of zones or levels of training intensity expressed in terms of such physiological domains. Such zones or training intensities may be further designed to fall within a range of specified heart rates that coincide with an individual's Anaerobic Threshold, Respiratory Compensation Point and $VO_2$max.

10 Claims, 6 Drawing Sheets

| | | Zone 1 | Zone 2 | Zone 3 | Zone 4 |
|---|---|---|---|---|---|
| | | 85.94% AT | 94-105% AT | 105% AT -50%Δ | 50%Δ-PEAK |
| | | 136 | 144 | 157 | 168 |
| Week | Duration | 144 | 153 | 168 | 178 |
| 1 | | | | | |
| a | 20 | 100% | 0% | 0% | 0% |
| b | 20 | 100% | 0% | 0% | 0% |
| c | 20 | 100% | 0% | 0% | 0% |
| 2 | | | | | |
| a | 22 | 90% | 10% | 0% | 0% |
| b | 22 | 90% | 10% | 0% | 0% |
| c | 22 | 90% | 10% | 0% | 0% |
| 3 | | | | | |
| a | 25 | 80% | 20% | 0% | 0% |
| b | 25 | 80% | 20% | 0% | 0% |
| c | 25 | 80% | 20% | 0% | 0% |
| 4 | | | | | |
| a | 28 | 70% | 25% | 5% | 0% |
| b | 28 | 70% | 25% | 5% | 0% |
| c | 28 | 70% | 25% | 5% | 0% |
| 5 | | | | | |
| a | 31 | 60% | 40% | 0% | 0% |
| b | 31 | 40% | 50% | 10% | 0% |
| c | 31 | 60% | 40% | 0% | 0% |
| 6 | | | | | |
| a | 34 | 40% | 60% | 0% | 0% |
| b | 34 | 30% | 50% | 20% | 0% |
| c | 34 | 40% | 50% | 10% | 0% |
| 7 | | | | | |
| a | 37 | 30% | 70% | 0% | 0% |
| b | 37 | 20% | 50% | 30% | 0% |
| c | 37 | 30% | 60% | 10% | 0% |
| 8 | | | | | |
| a | 40 | 20% | 70% | 10% | 0% |
| b | 40 | 20% | 50% | 30% | 0% |
| c | 40 | 20% | 60% | 20% | 0% |
| | TOTAL TIME | TIME IN EACH ZONE | | | |
| WEEK | (min) | Zone 1 | Zone 2 | Zone 3 | Zone 4 |
| WEEK 1 | 60 | 60 | 0 | 0 | 0 |
| WEEK 2 | 66 | 59 | 7 | 0 | 0 |
| WEEK 3 | 75 | 60 | 15 | 0 | 0 |
| WEEK 4 | 84 | 59 | 21 | 4 | 0 |
| WEEK 5 | 93 | 50 | 40 | 3 | 0 |
| WEEK 6 | 102 | 37 | 55 | 10 | 0 |
| WEEK 7 | 111 | 30 | 66 | 15 | 0 |
| WEEK 8 | 120 | 24 | 72 | 24 | 0 |

Fig. 5

| Habitual Activity | Fitness Level | Start Week |
|---|---|---|
| IA | L | 1 |
| MA | L | 2 |
| VA | L | 3 |
| IA | M | 1 OR 2 |
| MA | M | 4 |
| VA | M | 5 |
| IA | H | 3 |
| MA | H | 4 |
| VA | H | 8 |

Fig.6

SYSTEM AND METHOD FOR CARDIORESPIRATORY CONDITIONING

FIELD OF THE INVENTION

The present invention relates generally to methods and systems for the development and implementation of unique exercise regimens, and more particularly, methods and systems for developing customized cardiorespiratory fitness and endurance exercise programs for individuals.

BACKGROUND OF THE INVENTION

Exercise regimens for developing cardiorespiratory conditioning are known. The goal of such conditioning is to increase and sustain cardiac output, as well as develop the ability of the lungs to extract sufficient oxygen from the environment and to eliminate carbon dioxide which builds up as a result of increased muscle metabolism, to thus enable the individual to participate and/or compete in endurance sports, events, or activities such as distance running, cycling, rowing, soccer, etc.

To help achieve that end, the fitness industry, through the development of new exercise devices, has now made available to the general public a variety of means to exercise and become more physically fit. Among the more recent innovations include the development of programmable exercise devices, such as treadmills, stationary cycles, and stair climbers, which enable the user to "customize" a particular workout regimen based upon certain data provided by the user via a digital interface. Typically, the user must supply information regarding his or her weight, age, etc. which consequently causes the exercise device to implement an exercise regimen that strives to attain optimal cardiorespiratory conditioning, typically by maintaining the exercise regimen within the specified training intensity for a fixed duration.

Recent research tends to indicate that optimal cardiorespiratory conditioning occurs when an individual exercises at a training intensity at or above the Anaerobic Threshold (AT) (i.e., the point at which the subject can no longer provide all of the energy necessary to perform that workload with only aerobic metabolism). Because the terminology in the ever-evolving field of fitness is varied, it is understood in the art that the term Anaerobic Threshold may additionally be referred to as the Lactic Acid Threshold, Onset of Blood Lactate Accumulation (OBLA), Gas Exchange Threshold, Ventilatory Threshold, and/or Metabolic Acidosis Threshold. At exercise intensities above the AT, carbohydrates are anaerobically metabolized into lactic acid, as opposed to pyruvate under aerobic metabolism. While the body is able to clear (i.e., metabolize) some lactic acid, a point is eventually reached whereby the lactic acid begins to accumulate in the muscles and bloodstream, eventually causing muscle soreness and fatigue.

Novel research now tends to indicate that for the trained, highly-conditioned athlete cardiorespiratory conditioning can be achieved by exercising for short durations near the individual's Respiratory Compensation Point (RCP) (the point at which the individual is most physically active and is characterized by a marked increase in ventilation and $CO_2$ production) and, for the most well-conditioned athletes, near the individual's maximum oxygen consumption ($VO_2$max). When the individual exercises at or near his or her RCP, the excess of lactic acid produced by the muscles acidifies the blood and causes the individual to hyperventilate and expire as much $CO_2$ as possible. Eventually, the individual must default the exercise, typically within 60 to 120 seconds after having reached the RCP, particularly if the work rate continues to increase. To the extent the individual is capable of sustaining a greater work load during the individual's RCP, albeit for a very brief period, the individual eventually reaches his or her $VO_2$max, which coincides with the individual's inability to engage in any further physical activity insofar as the symptoms of exhaustion overwhelm the individual's system.

While methods are available for determining the point at which an individual reaches his or her Anaerobic Threshold and Respiratory Compensation Point, typically via gas exchange tests that detect an increase in expired minute ventilation (VE), oxygen uptake ($VO_2$) or carbon dioxide output ($VCO_2$), such tests have not heretofore been applied for purposes of constructing an exercise regimen centered around training intensities that specifically target the individual's Anaerobic Threshold and Respiratory Compensation Point, let alone identify specific durations at which a given exercise is to be performed at a given training intensity. In this respect, the relative inaccessibility of the sophisticated equipment and trained staff needed to conduct aerobic fitness tests, interpret the results, and use these results to develop rational training programs has prevented the widespread use of scientific knowledge among those wishing to optimize their aerobic fitness.

In an attempt to provide some objective standard, guidelines from the American College of Sports Medicine (ACSM) have suggested training intensities based on percentages of maximal oxygen uptake ($VO_2$max), percentages of the heart rate (HR) reserve (HRres, which is HRmax-HRrest), or percentages of HRmax, which typically fall within the range from 40–90% of these variables. To date, however, no explicit guidelines have been determined regarding which percentage or individual state of training is best for whom, and under what training conditions. For example, two people could both be given a training intensity of 70% of the HRres. One individual might carry out this recommendation within the aerobic domain (below the lactic acidosis threshold) while the other person might be above it. While both people train at the same percentage of the HRres, each experiences a different metabolic requirement for adenosine triphosphate (energy) production. One may be able to sustain the activity quite a bit longer (below the Anaerobic Threshold) while the other will be limited in his/her ability to continue work by lactic acid accumulation. As such, issues arise as to whether both people are training at the same intensity.

Further compounding the difficulties in prescribing exercise intensities is the common practice of estimating the maximum heart rate for use in generating a training heart rate (THR). One approach to this calculation is the 220-minus-age method. However, the error associated with this estimate has been reported as 10–15 beats per minute.

Some practitioners prescribe exercise intensities on the basis of a percentage of $VO_2$max. Often (if not usually) $VO_2$max is not actually measured in the fitness center or health club setting. Rather, $VO_2$max is estimated from the heart rate-work rate (WR) relationship obtained from a sub-maximal test. Maximal work rate is then predicted by extrapolating the HR-WR curve to an estimated (i.e., 220 minus age) HRmax. Errors in estimating $VO_2$max by this approach average about 15% and have been reported to be as high as 25%.

In this regard, if maximal HRs are distributed normally in the population, the mean (average) HR will occur at 220 minus age. One standard deviation (SD) from this mean would be ±10 beats per minute. For example, a 30-year-old would have a predicted HRmax of 220 minus 30 or 190 beats per minute. Statistically, 68% of these people aged 30 would have a maximal HR between 180 and 200 beats per minute. However, this range does not include the remaining 32% of people 30 years of age. Moving out two standard deviations will capture more 30-year-olds (95% of the population), but the range of HRmax will now increase and by 10 more beats per minute on each side of the mean, yielding 170–210 beats per minute. At this point, approximately 5% of the 30-year-old population would still not be accounted for. Moving out one more standard deviation will include 99% of the population, but the range of HRmax would fall between 160–220 beats per minute. As a consequence, for every 100 people of age 30 encountered, roughly 68 of them will have a HRmax between 180 and 200 beats per minute.

To illustrate this concept, if a resting HR (HRrest) of 70 beats per minute is assumed, the familiar Karvonen formula (220 minus age) and an arbitrary intensity value of 70% of the HRrest would yield a training heart rate of 154 beats per minute for the average 30-year-old. An error up to 1 SD from the mean would over- or under-estimate the THR by ±7 beats per minute. However, the farther the movement away from the mean, the greater the error. Even at ±2 SD from the mean, the THR error is ±14 beats per minute and ±21 beats per minute for the rare individual who is ±3 SD from the mean.

As opposed to the aforementioned methodology using assumptions or estimates for implementing exercise regimens at specified training intensities, attempts have been made to personally assess cardiorespiratory fitness and construct individual training programs based upon such evaluation.

The most typical cardiorespiratory fitness test used in health clubs and fitness centers is the sub-maximal cycle ergometer test. Such standardized test, however, is problematic for several reasons. First, use of the cycle ergometer may violate the law of specificity in that not all individuals who undergo a cycle ergometer test will train on the cycle ergometer. Thus, the extent to which a person improves aerobic capacity may not be truly identified if the individual uses a different mode of exercise for training, such as jogging. Second, sub-maximal tests have potentially large errors in predicting VO$_2$max, namely, the maximal amount of oxygen that can be used for energy production during exhaustive exercise. The VO$_2$max occurs beyond RCP and is a measure of the individual's endurance exercise capacity and cardiorespiratory functional capacity. Third, identification and use of the Anaerobic Threshold is impossible without either blood samples analyzed for lactic acid or measurements of gas exchange. As such, due to the unique physiological responses of every individual, coupled with the different types of physical conditioning provided by different types of exercise equipment, an exercise regimen that truly optimizes cardiorespiratory fitness is rarely, if ever, implemented.

Separate and apart from the foregoing, the ideal approach would be to customize or specifically tailor an exercise regimen using identifiable training intensities based upon an individual's specific cardiorespiratory function, as identified by the specific physiological markers unique to that individual. As discussed above, studies investigating intensities of training typically report that the greatest improvements in aerobic function occur at the highest training intensities. Nevertheless, unanswered questions still persist as to what training intensity brings optimal results, how training intensity should be determined and manipulated, and whether one training intensity is appropriate for optimal benefit. Accordingly, there is a need in the art for systems and methods for assessing an individual's cardiorespiratory fitness and determining the specific training intensities that the individual can strive for that optimize his or her cardiorespiratory conditioning. There is further a need in the art for systems and methods for not only identifying such training intensities, but for exercise regimens that are centered around such training intensities that can be utilized to more rapidly increase endurance and cardiorespiratory conditioning than prior art methods. There is still further a need in the art for systems and methods for exercise regimens utilizing training intensities that are custom tailored to suit the needs of a particular individual that can be applied to any of a variety of cardiorespiratory exercise devices, including, but not limited to treadmills, stationary bicycles and/or stair climbers.

SUMMARY OF THE INVENTION

The methods and systems of the present invention specifically address and alleviate the aforementioned problems. In this regard, the present invention is directed to systems and methods for accurately assessing cardiorespiratory fitness by identifying the specific and individual exercise domains as identified by Anaerobic Threshold and Respiratory Compensation Point and, based upon such determination, formulating exercise training regimens that are more effective and customized to fit the particular needs of an individual.

According to the preferred embodiment, the Anaerobic Threshold is identified by the so-called "dual criteria" in which the ratio of the expired minute ventilation ($V_E$) to the individual's oxygen uptake ($VO_2$), i.e., $V_E/VO_2$ (the ventilatory equivalent for oxygen) increases while at the same time, the ratio of $V_E$ to the individual's carbon dioxide output ($VCO_2$), i.e. $V_E/VCO_2$, (the ventilatory equivalent for $CO_2$) does not increase during the performance of exercise having a gradually increasing intensity. The Anaerobic Threshold can further be determined by the increase in carbon dioxide output relative to the increase in oxygen uptake during such progressively intense exercise. Known as the V-slope method, the Anaerobic Threshold is ascertained by identifying the point at which $CO_2$ output starts to increase more rapidly than the increase in oxygen uptake (which is indicative of the individual's attempt to buffer the accumulating lactic acid with bicarbonate which, in the process, is converted to $CO_2$).

Once the Anaerobic Threshold has been determined, a further determination is made regarding the individual's Respiratory Compensation Point, which is identified as the point where an individual experiences a marked increase in ventilation and $CO_2$ output during strenuous exercise due to hyperventilation in response to the metabolic acidosis. Generally, such exercise activity produces an excess of lactic acid which overwhelms the system and causes the individual to hyperventilate to thus expire as much $CO_2$ as possible. Typically, the individual is only capable of performing such exercise for 60 to 120 seconds before defaulting due to exhaustion.

Optionally, to the extent the individual is physically capable, such individual's VO$_2$max is determined by further increasing the work load or intensity of a particular exercise after the individual has reached his or her Respiratory Compensation Point until such time as the individual is incapable of performing any further physical activity due to having been overwhelmed from fatigue and exhaustion. Once the AT, RCP, and (optionally) $VO_2$max, have been ascertained, as well as the individual's corresponding heart rate associated with such markers, an exercise regimen is then constructed. Preferably, the exercise regimen comprises a multiplicity of scheduled exercises wherein each exercise has at least one, and preferably two or more zones of training intensity that cause the individual performing such exercise to maintain his or her heart rate at a rate corresponding to a percentage of the Anaerobic Threshold, Respiratory Compensation Point, and/or $VO_2$max physiological markers. In this regard, the percentages of the individual's heart rate, and more particularly the $O_2$ uptake relative to such physiological markers can be utilized to establish different dynamic energy metabolism zones to establish cardiorespiratory exercise programs that are unique to that individual and maximize cardiorespiratory conditioning.

The present invention further contemplates that once such metabolically-based heart rate zones (i.e., the heart rate zones based upon and linked to the Anaerobic Threshold and RCP) and their corresponding caloric expenditure have been established, a periodized, systematic exercise conditioning program can be designed. In this respect, such measurements provide the basis for a physiologically justifiable approach to training by identifying clear-cut domains of exercise tolerance around which training guidelines may be established to develop endurance for specific sports or events such as distance running, cycling, rowing, soccer, triathlon, etc. Preferably, such exercise regimen would comprise the initial step of identifying an individual's baseline fitness level and performing exercises in a routine basis in specific intensity or training zones for specified durations with the systematic increase in training intensities and duration at a graduated rate to ultimately achieve the most efficient rapid physiological adaptation to exercise.

BRIEF DESCRIPTION OF THE DRAWINGS

These, as well as other features of the present invention will become more apparent upon reference to the drawings wherein.

DETAILED DESCRIPTION OF THE PREFERRED EMBODIMENT

The detailed description as set forth below in connection with the appended drawings is intended as a description of the presently preferred embodiments of the invention, and is not intended to represent the only form in which the present invention may be constructed or utilized. The description sets forth the functions and sequences of steps for constructing and operating the invention in connection with the illustrated embodiments. It is understood, however, that the same or equivalent functions and sequences may be accomplished by different embodiments and that they are also intended to be encompassed within the scope of this invention.

The systems and methods of the present invention are directed to means for measuring cardiorespiratory fitness and identifying optimal exercise intensity levels that are best suited for a particular individual. In this regard, such exercise or training intensities are selectively established so that the individual maintains an exercise activity at a specified level or zone for a fixed duration of time that is known to correspond to a certain percentage of that individual's Anaerobic Threshold, Respiratory Compensation Point and/or $VO_2$max. These training intensity levels may be set to coincide with certain specified ranges of heart rates of the individual that correspond to the individual's Anaerobic Threshold, Respiratory Compensation Point, or $VO_2$max.

Accordingly, it will be recognized at the outset that before such exercise regimen can be constructed, at least one and preferably two key metabolic measurements used to construct the heart rate zones, namely, the Anaerobic Threshold (AT) and Respiratory Compensation Point (RCP) must first be identified. Because the systems and methods of the present invention are based primarily on the Anaerobic Threshold, it should be understood that proper identification of this threshold is of paramount importance. To that end, it is contemplated that a variety of methods (e.g., blood tests) may be utilized to determine a particular individual's Anaerobic Threshold, which as used herein is defined as a readily identifiable metabolic phenomenon that occurs within an exercising individual that is characterized by the accumulation of lactic acid in the muscles and bloodstream, increase ventilatory volume and expired $CO_2$. It should be understood at the outset, however, that the term Anaerobic Threshold is additionally referred to in the art as either the Lactic Acid Threshold, Onset of Blood Lactate Accumulation (OBLA), Gas Exchange Threshold, Ventilatory Threshold, and/or Metabolic Acidosis Threshold. Accordingly, it should be understood that all of these terms are to be deemed the equivalent of Anaerobic Threshold.

For purposes of the present invention, however, it is believed that the Anaerobic Threshold may be readily detected by gas exchange ($AT_{GE}$) by noting the increase in the individual's $CO_2$ output relative the individual's $O_2$ uptake or, alternatively, an increase in the individual's expired minute ventilation relative the individual's $O_2$ uptake. Either such gas exchange method is based upon the well-established fact that lactic acid, being an acid, is buffered in the body by bicarbonate ($HCO_3-$) to form carbonic acid ($H_2CO_3$) which in turn dissociates into carbon dioxide and water. These compounds travel in the bloodstream to the lungs where the additional $CO_2$ appears in the breath of the individual and can be measured as $VCO_2$. As such, an excess of $CO_2$ appears in the breath of the individual and can be measured as $VCO_2$. Additionally, the minute ventilation of such individual is increased in order to get rid of the excess $CO_2$ and this increase can be measured. The individual's $O_2$ uptake during such metabolic phenomenon, however, has remained firmly and predictably linked to the external work rate and thus provides a benchmark by which such increases can be ascertained. The principles regarding the physiology and biochemistry associated with the consumption of oxygen during increasing intensities of exercise are discussed at length in the *Handbook of Gas Exchange and Indirect Calorimetry*, and Howley, et al. "Criteria For Maximal Oxygen Uptake: Review and Commentary" in the *Official Journal of the American College of Sports Medicine* (1995), the teachings of which are expressly incorporated herein by reference.

Generally, the approaches used to identify the thresholds for AT and RCP via gas exchange are identified below in Table 1.

TABLE 1

THRESHOLD IDENTIFICATION METHODS

| | AT | RCP |
|---|---|---|
| Primary Method | $VCO_2$ v. $VO_2$ plot (V-slope) | $V_E$ v. $VCO_2$ plot |
| Additional Method #1 | *$V_E/Vo_2$ v. $VO_2$, work rate or time (dual criteria) | $V_E/VCO_2$ v. $VO_2$, work rate or time |
| Additional Method #2 | $PETO_2$ v. $VO_2$, work rate or time (dual criteria) | $PETCO_2$ v. $VO_2$, work rate or time |

*This part of the methodology utilizes the principle of "dual criteria" whereby the Anaerobic Threshold or AT is selected at the inflection point on the plot of $V_E/VO_2$ but reference is also made simultaneously to the plot $V_E/CO_2$ to verify that the former is changing while the latter remains relatively constant.
**This part of the methodology utilizes the principle of "dual criteria" whereby the Anaerobic Threshold or AT is selected at the inflection point on the plot of $PETO_2/VO_2$ but reference is also made simultaneously to the plot $PETCO_2/VCO_2$ to verify that the former is changing while the latter remains relatively constant.

Figure 1:
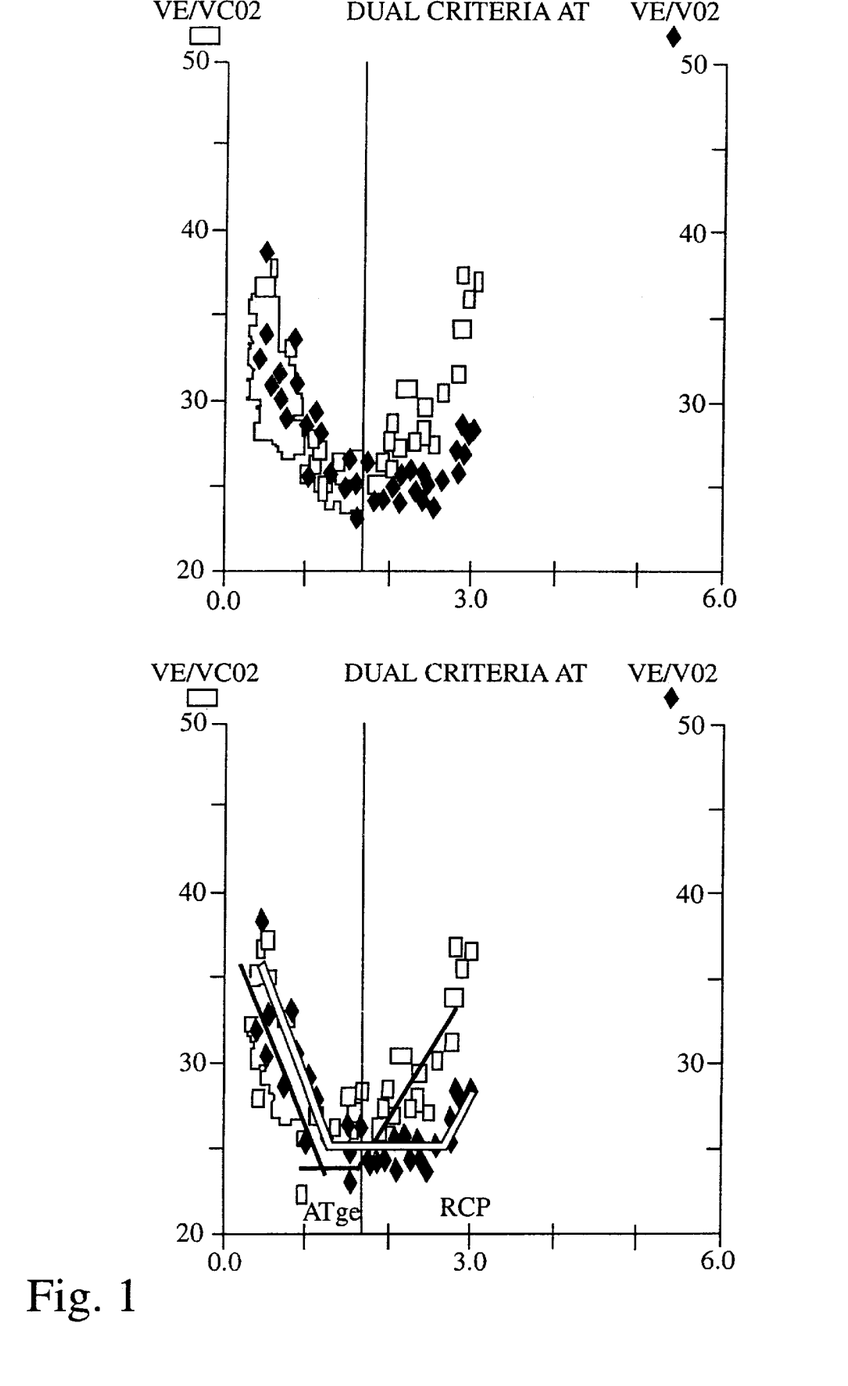
FIG. 1 depicts a dual-criterion plot comparing an individual's expired minute ventilation ($V_E$) to the individual's $O_2$ uptake ($VO_2$), i.e., $V_E/VO_2$, during the performance of an exercise having an increasing training intensity with the ratio of expired minute ventilation to oxygen uptake, relative to the ratio of the individual's $V_E$ to $CO_2$ output ($VCO_2$), i.e. $V_E/VCO_2$, being utilized to determined the individual's Anaerobic Threshold.

With respect to the preferred method of determining an individual's Anaerobic Threshold by comparing minute ventilation versus $O_2$ uptake, there is illustrated a dual criterion plot shown in FIG. 1. Generally, to detect $AT_{GE}$ typically requires the formation and evaluation of $V_E/VO_2$ and $V_E/VCO_2$ vs. $VO_2$ (Dual Criterion Plot). Initially, three phase responses (i.e., curves) of both $V_E/VO_2$ and $V_E/VCO_2$ are observed. Both curves should start relatively high, fall and level off at about 23–27 for $V_E/VO_2$ and 25–29 for $V_E/VCO_2$, then rise, with the increase in $V_E/VO_2$ occurring before that of $V_E/VCO_2$. Thereafter, the Respiratory Compensation Point (RCP) is identified. This is the point at which the $V_E/VCO_2$ begins to rise near the end of the curve. $AT_{GE}$ must be before (i.e., to the left) of this point. The curve of $V_E/VO_2$ is then examined noting where the same falls and subsequently levels off, and the points exhibiting a leveling with a horizontal line are identified. Note the point at which $V_E/VO_2$ begins to systematically rise. This is the $AT_{GE}$ if the $V_E/VCO_2$ curve is still level. It should additionally be recognized that in some subjects, the $V_E/VO_2$ curve will exhibit more of a fall and subsequent rise rather than a true leveling off. In this case, identify the nadir (i.e., the lowest point) and mark the point at which the curve systematically turns upward as the AT.

Moreover, it is contemplated that for individuals already training, the incremental exercise test from which AT and RCP are identified may be further increased to the point where the individual experiences exercise intolerance or volitional fatigue. Such point coincides with the individual's maximum oxygen consumption ($VO_2$max). Technically, the maximum value of $VO_2$ measured during a symptom-limited, incremental exercise test, might not be the true maximal value which that individual could achieve in ideal circumstances. Hence, some professionals refer to the highest measured value of $VO_2$ as $VO_2$peak. It should be recognized that such third metabolic marker (i.e., $VO_2$max), while capable of being measured in any individual, should typically only be ascertained in those individuals that have a relatively good degree of cardiorespiratory conditioning and are capable of engaging in such activity.

Figure 2:
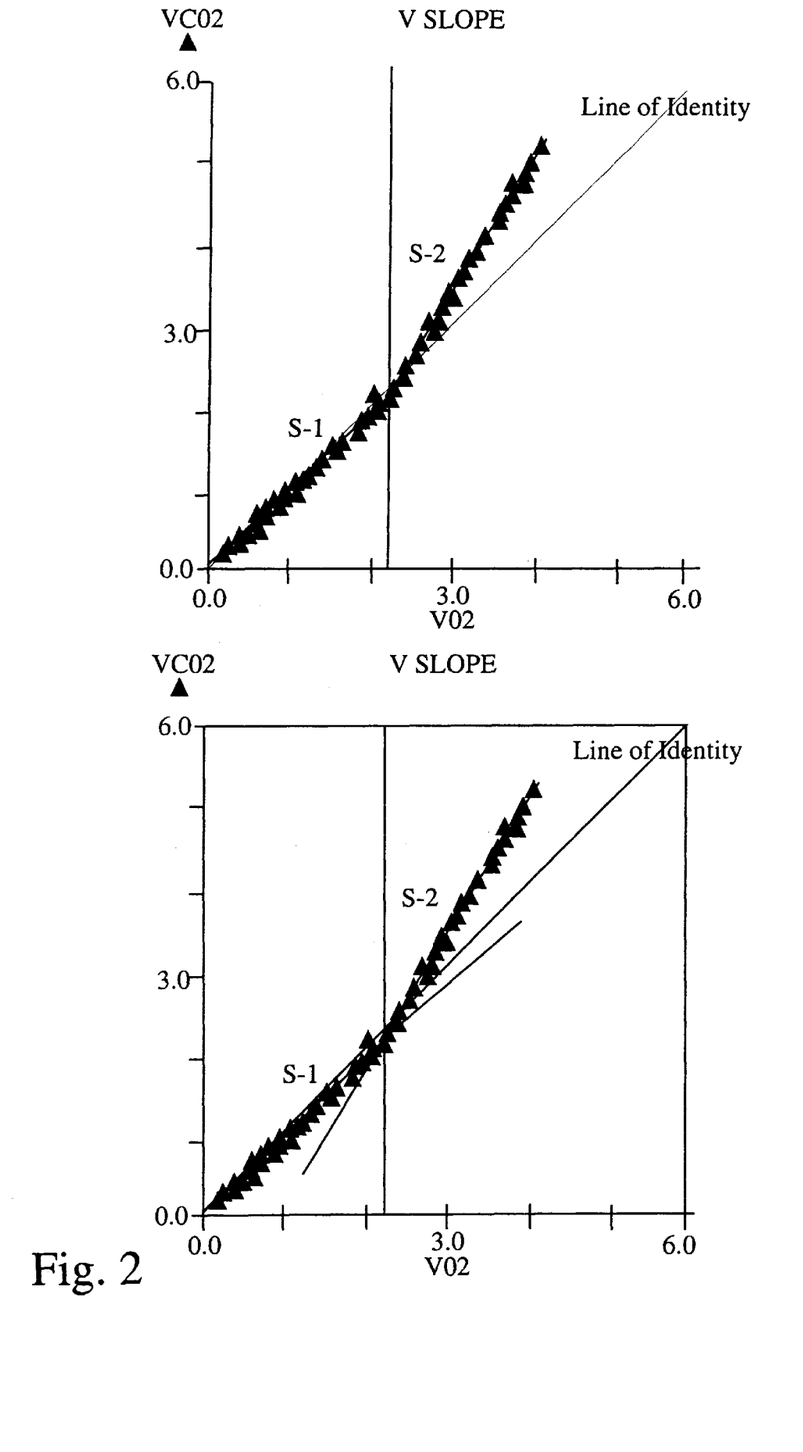
FIG. 2 depicts a V-slope plot comparing an individual's output of carbon dioxide versus oxygen uptake during the performance of an exercise having an increasing training intensity with the ratio of carbon dioxide output to oxygen uptake being utilized to determined the individual's Anaerobic Threshold.

Alternatively, as depicted in FIG. 2, there is shown a plot of $CO_2$ output versus $O_2$ uptake ($VCO_2$ versus $VO_2$) that may be utilized to determine the Anaerobic Threshold of a particular individual. Such plot, known as a V-slope plot, identifies the Anaerobic Threshold based upon the increase in $CO_2$ production that occurs relative $O_2$ uptake that occurs at the Anaerobic Threshold as lactic acid converts to carbonic acid and ultimately water and $CO_2$, the latter of which is eliminated in detectably greater quantities. During aerobic activity, the initial rise in $CO_2$ output ($VCO_2$) is fairly linear with respect to $VO_2$. The slope of the $VCO_2$ curve during this phase of exercise is parallel with the line of identity, indicating that no excess $CO_2$ is being produced. This first slope is referred to as S-1. At the Anaerobic Threshold, the rate of increase in $CO_2$ is accelerated due to the lactic acid buffering and the excess $CO_2$ produced from this process as discussed above. Graphically, a distinct steepening of this curve occurs, and is identified as the second slope (S-2). As will be appreciated, the transition between slopes S-1 and S-2 mark the Anaerobic Threshold, and can be identified on the plot shown as the point where the $VCO_2$ to $VO_2$ ratio transitions between slope 1 and slope 2. Technically, the $AT_{GE}$ is the point at which S-1 and S-2 intersect. To facilitate the identification of the Anaerobic Threshold, S-1 and S-2 may be extrapolated so that the intersection between the two may be readily identified and documented. Similar to the first method for ascertaining $AT_{GE}$, the procedure is then further conducted to determine the Respiratory Compensation Point. The Respiratory Compensation Point is best identified from the plot of $V_E$ versus $VCO_2$ but can also be identified by inflections in the plot of $V_E/VCO_2$, $VO_2$, work rate or time, or the plot of end-tidal $CO_2$ plot versus $VO_2$, work rate or time. Optionally, the individual's $VO_2$max may additionally be determined by increasing the exercise intensity being performed by the individual to a point where the individual experiences exercise intolerance.

While it is recognized that some subjectivity is inherent in the aforementioned processes, each of the aforementioned has been documented to identify the Anaerobic Threshold accurately. Currently, it is believed that the V-slope technique depicted in FIG. 2 provides the most reliable data from which such metabolic marker may be identified. Moreover, it should be recognized that in any of the aforementioned methods, the specific metabolic markers may be identified by any of a variety of graphical methods, including, but not limited to, by visual inspection (i.e., hand drawing of lines of best fit, and a determination of their intersection point), by linear regression analysis of different sections of the plot above and below the putative threshold, by linear regression of the entire data set and determination of the point of farthest deviation from that line of best fit, and/or by any mathematical or geometric method.

Advantageously, however, since oxygen uptake may be measured directly throughout the exercise test, no estimation of $VO_2$ is required. Thus, any exercise device may be used for the incremental exercise test. Test and training mode specificity can therefore be maintained. Errors in predicting $VO_2$max are eliminated when a peak exercise test is performed using the instrumentation and software of the present invention. Moreover, AT can be accurately and reliably detected using analysis of the gas exchange responses to exercise conducted with the present invention.

Figure 3:
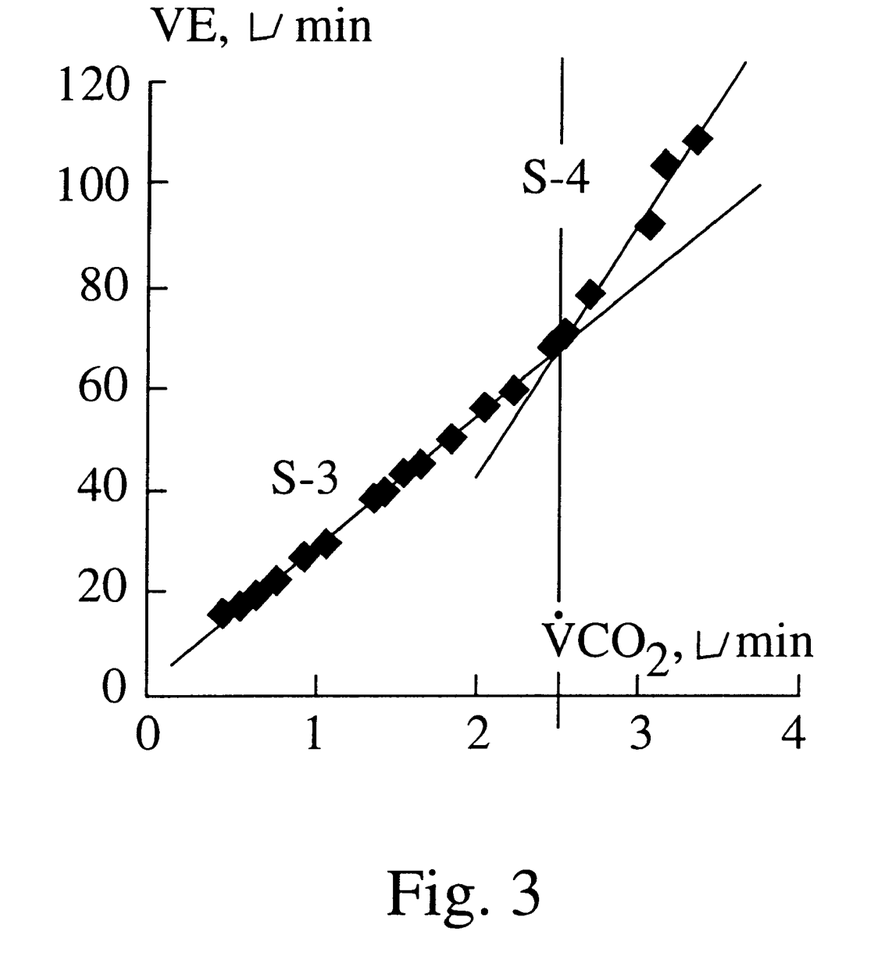
FIG. 3 depicts a plot of expired minute ventilation versus $CO_2$ output useful in determining an individual's Respiratory Compensation Point.
Figure 4:
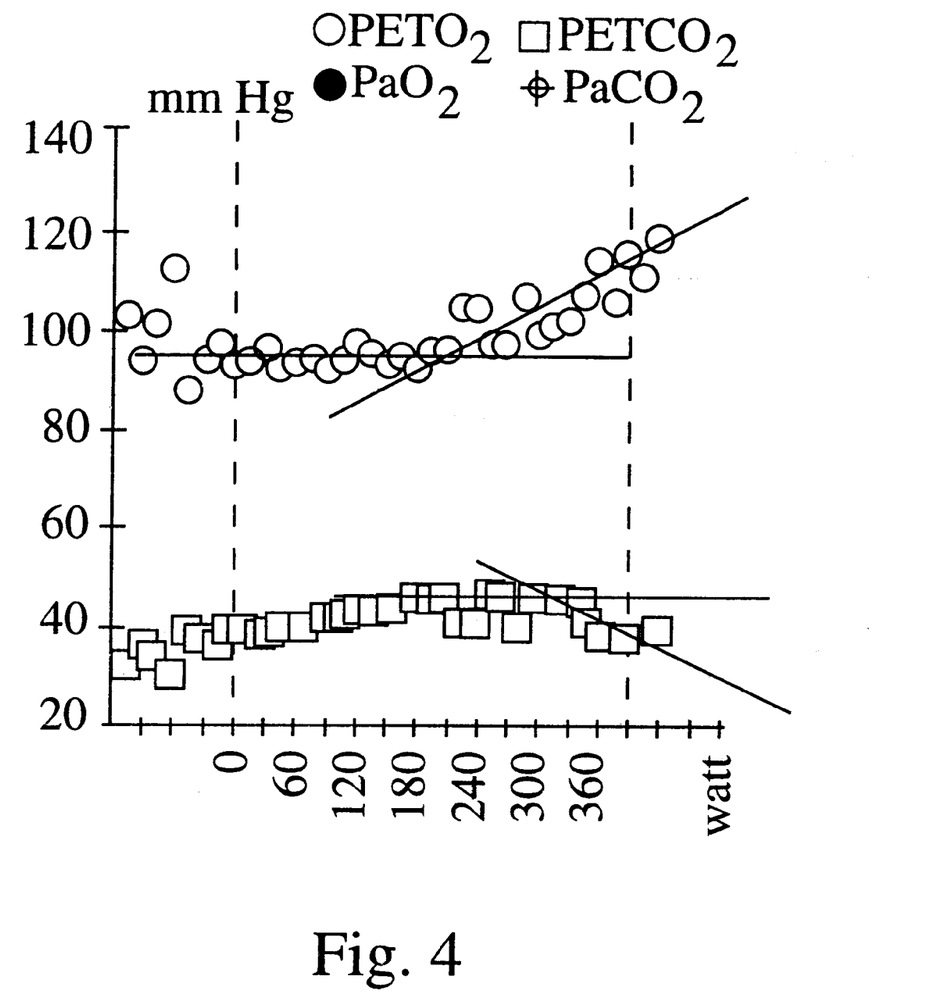
FIG. 4 depicts an end-tidal gas tension ($PETO_2$ and $PETCO_2$, the partial pressures of end-tidal $O_2$ and $CO_2$, respectively) versus oxygen uptake plot useful in determining an individual's Anaerobic Threshold and Respiratory Compensation Point.

Along these lines, it will further be recognized that yet another way to determine an individual's Anaerobic Threshold and Respiratory Compensation Point is through the formation of end-tidal gas tensions versus $O_2$ uptake plot, as depicted in FIG. 3. Such plot, which is derived from Karlman Wasserman, M.D., Ph.D. et al., *Principles of Exercise Testing and Interpretation* (1994) illustrates an end-tidal gas tension ($PETO_2$ and $PETCO_2$, the partial pressures of end-tidal $O_2$ and $CO_2$, respectively) versus oxygen uptake plot useful in determining an individual's Anaerobic Threshold and Respiratory Compensation Point. Similarly, a yet further alternative method for determining the Respiratory Compensation Point in an individual is through the formation of a plot of expired minute ventilation (i.e., $V_E$) versus $CO_2$ output (i.e., $VCO_2$), as depicted in FIG. 4. With respect to the latter, such Figure is again derived from Wasserman, et al., *Principles of Exercise Testing and Interpretation* (1994) which depicts a plot of expired minute ventilation versus $CO_2$ output useful in determining an individual's Respiratory Compensation Point. As will be recognized by those skilled in the art, such measurements may be obtained by any of a variety of conventional respiratory measuring and monitoring equipment, such as those produced by Sensormedics, Inc. of Yorba Linda, Calif.

In addition to documenting the AT, RCP, and (optionally) $VO_2$max via the aforementioned methods, it is further important that the corresponding heart rates for the individual at such physiological markers be identified for use in developing the customized exercise regimes discussed more fully below. In this regard, by utilizing the heart rate of the individual that coincides with the individual's Anaerobic Threshold, RCP and $VO_2$max, it is believed that exercise regimens can be developed and implemented that develop superior cardiorespiratory conditioning based upon the individual performing exercise activities at specified intensity levels as a function of the individual's AT, RCP and $VO_2$max, as those physiological parameters are expressed in terms of heart rate.

As will be appreciated by those skilled in the art, there has not heretofore been available any exercise regimens or training schemes that have set training intensity levels that elicit physical performance that falls within at least one, let alone three, specific, readily-identifiable physiological domains that are unique to a given individual. In this regard, with the determination of an individual's AT, RCP and $VO_2$max, certain training intensities or dynamic metabolically-based zones can be designed for any of a variety of exercises, whether it be jogging on a treadmill, or riding a stationary bike, such that when the individual performs such exercises the individual's metabolism operates either below the Anaerobic Threshold, between the Anaerobic Threshold and the Respiratory Compensation Point, and between the Respiratory Compensation Point and the individual's $VO_2$max. Indeed, such training intensities or zones can be expressly formulated so that the individual is caused to respire or function at a certain metabolic level within one of the three aforementioned physiological domains for a fixed duration. As a consequence, any exercise regimen implemented by utilizing such identifiable metabolic markers insures that the individual performing such exercises actually functions within his or her known physiological domains for specified durations. No exercise program to date has been known to elicit such an objectively identifiable exercise performance.

In addition to the foregoing, it will further be appreciated by those skilled in the art, by expressing an individual's Anaerobic Threshold, Respiratory Compensation Point and $VO_2$max in terms of specific heart rates, the individual thus will be provided with an easily ascertainable and readily identifiable physiological parameter that can be attained and monitored for specified durations via a specified level of training intensity, discussed more fully below. For example, if an individual has a heart rate of 170 at his or her Anaerobic Threshold, adjustments can be made such that the individual performs a given exercise, whether it be cycling, jogging, etc. such that the heart rate of the individual is maintained at 170 or a percentage thereof for a given duration. Of additional advantage, because a wide variety of available fitness equipment available provides means for measuring heart rate, expressing AT and $VO_2$max in terms of heart rate can provide the user with means to selectively adjust his or her workout so that optimal cardiorespiratory conditioning attained.

As an alternative to utilizing corresponding heart rates of the individual's AT, RCP and/or $VO_2$max, it should additionally be understood that the individual's $O_2$ uptake at such specific physiological markers may also be utilized in formulating the exercise regimens discussed more fully below. In this regard, it should be understood that the individual's specific $O_2$ uptake can be measured and identified at such markers via graphical determination. Advantageously, by using the individual's $O_2$ uptake at the various physiological markers, a determination can further be made with respect to caloric expenditure at such various physiological markers. Moreover, by providing a corresponding $O_2$ uptake with the individual's heart rate at such specific physiological markers, a determination can further be made as to the caloric expenditure of the individual per heart beat. In this regard, it is contemplated that an individual's $O_2$ uptake can be plotted against the individual's heart rate so that a variety of graphics can be generated and data derived therefrom to indicate incremental changes in caloric expenditure per heart beat as the individual's heart rate varies during a given exercise activity. Unlike any prior art exercise program, the exercise regimens and methodology of the present invention allow for a specific identification of the calories consumed per heart beat unique to each individual.

With respect to implementing an exercise focusing upon the unique physiological domains of a given individual, it is presently contemplated that such exercise regimen will be comprised of a multiplicity of exercise activities wherein each activity is performed at at least one intensity level or zone known to fall within one of the three physiological domains of the individual. Preferably, two or more training intensities or zones are established that cause the individual to respire at differing levels within a given physiological domain, or even operate at certain levels within two or more physiological domains for certain fixed durations. Specifically, it is contemplated that a first zone or training intensity may be established that causes the individual to engage in an activity that elicits an oxygen uptake or heart rate falling within a range of percentages of the individual's oxygen uptake or heart rate at his or her Anaerobic Threshold, for example, 70% to 100%, and that a second training intensity or zone may further be established that elicits an oxygen uptake or heart rate falling within a second or higher range of percentages of the individual's Anaerobic Threshold oxygen uptake or heart rate, for example, 90% to 120%.

Similarly, training intensities or zones can be established with respect to the other physiological markers. Indeed, three, four, five or even more zones may be established that elicit from the individual an exercise performance which causes the individual to achieve a metabolic rate falling within one of the three physiological domains for fixed durations. As will be recognized, the training intensities or zones can be expressed as a function (i.e., percentage) of the individual's oxygen uptake or heart rate at either of the individual's Anaerobic Threshold, Respiratory Compensation Point, and/or $VO_2$max. Moreover, as identified above, such training intensities or zones may be expressed in terms of percentages of the individual's heart rate at either of the individual's AT, RCP and/or $VO_2$max.

In this regard, it is presently contemplated that exercise regimens can be established for individuals who are not physically fit by merely identifying a given individual's Anaerobic Threshold and the corresponding heart rate thereat, and thereafter scheduling a series of exercises wherein the activity of such exercises elicits from the individual a heart rate or oxygen uptake, which can also be expressed as a heart rate, that can fall anywhere within the range (e.g., 50% to 200%) of the individual's oxygen uptake or corresponding heart rate at his or her Anaerobic Threshold. To the extent the individual is capable of engaging in physical activity that elicits a heart rate falling within higher levels of the individual's physiological domains (closer to the individual's Respiratory Compensation Point), the HR boundaries for one or more training zones or intensity levels are constructed. The fitness professional may then partition the client's training time (duration) into one or more of the zones depending upon any or all of the following factors:

1. Habitual training.
2. Age.
3. Health status and risk factors.
4. Fitness or performance goals.
5. Stage in the long-term training progression.

With respect to the various training intensities or zones, it is contemplated that any such zones may encompass any type of training intensity that elicits a known range of heart rates or $O_2$ uptakes relative to any of the three aforementioned metabolic markers (i.e., AT, RCP and/or $VO_2$max). It should be understood, however, that the purpose of such zones is to provide incremental steps within an exercise regimen that correspondingly produce either an increase or decrease in an individual's heart rate or $O_2$ uptake relative to any of the aforementioned metabolic markers. Presently it is believed that zones can be constructed that can range anywhere from the $O_2$ uptake or heart rate at 50% of an individual's Anaerobic Threshold up to the heart rate or $O_2$ uptake of the individual's $VO_2$max. It should be understood that this upper limit may also be expressed in terms of percentages of the individual's Anaerobic Threshold or RCP, and it is believed that an upper range of 200% of an individual's heart rate or $O_2$ uptake at his or her Anaerobic Threshold can be used as a general guideline to represent a hypothetical upper limit for exercise training.

With respect to the periodization of an individual exercise program regarding a given training intensity or zone, it is presently contemplated that certain mathematical formulas can be derived that, in addition to identifying which zone or zones are appropriate for a given individual based upon the individual's metabolic markers, further provide specified durations that the individual performs such exercises (expressed in terms of minutes), as well as the frequency such exercises are performed in a given period of time (e.g., three to four times per week).

Once the measurements for determining training intensities has been identified, the intensity of training may be varied as the client adapts to the new exercise routine, and periodizing the training with respect to intensity, duration and frequency. By way of example, there is illustrated in FIG. 3 an eight-week progressive training program for an inactive person utilizing four training zones. For each of the eight weeks, a, b, and c represent three different training days, e.g., Monday, Wednesday, and Friday (more days could be added at the discretion of the fitness professional). Duration of training (minutes per day) are given for each week, progressing 10% per week from 20 minutes to 40 minutes over the eight weeks. Within each week after week 1, the total training time is partitioned among the three or four zones as appropriate for the client. This, too, is progressed over the eight weeks with more time at higher intensities. After eight weeks of training, the fitness professional may wish to consider a re-evaluation in order to update the heart rate zones since very likely, $VO_2$ at AT and $VO_2$peak will have improved.

With respect to those individuals having varying degrees of habitual activity and fitness levels, it is contemplated that specified intensities, durations and frequencies can be assigned to such individuals so that the exercise regimens of the present invention can be utilized to build upon pre-established cardiorespiratory conditioning. As illustrated in FIG. 6, there is shown an intensity duration and frequency chart utilized to assign particular exercise regimens as set forth in FIG. 5. As illustrated, two factors are taken into account, namely, habitual activity and fitness level, in determining at what week the individual is to commence the practice of the prescribed exercises. In this regard, habitual activity is identified as either inactive (IA), moderately active (MA), or very active (VA). Fitness levels are characterized as either low (L), medium (M), or high (H). To the extent an individual is inactive (IA) and has a low fitness level (L), the individual would start the eight-week program identified in FIG. 5 at Week 1. On the other hand, to the extent an individual is very active (VA) and has a moderate fitness level (M), such individual would begin the exercise regimen as set forth at Week 5 of the scheme illustrated in FIG. 5. As such, optimal conditioning can begin right away and therefore progress at a more rapid pace than would occur should an active individual having a high fitness level begin at Week 1.

Figure 5:
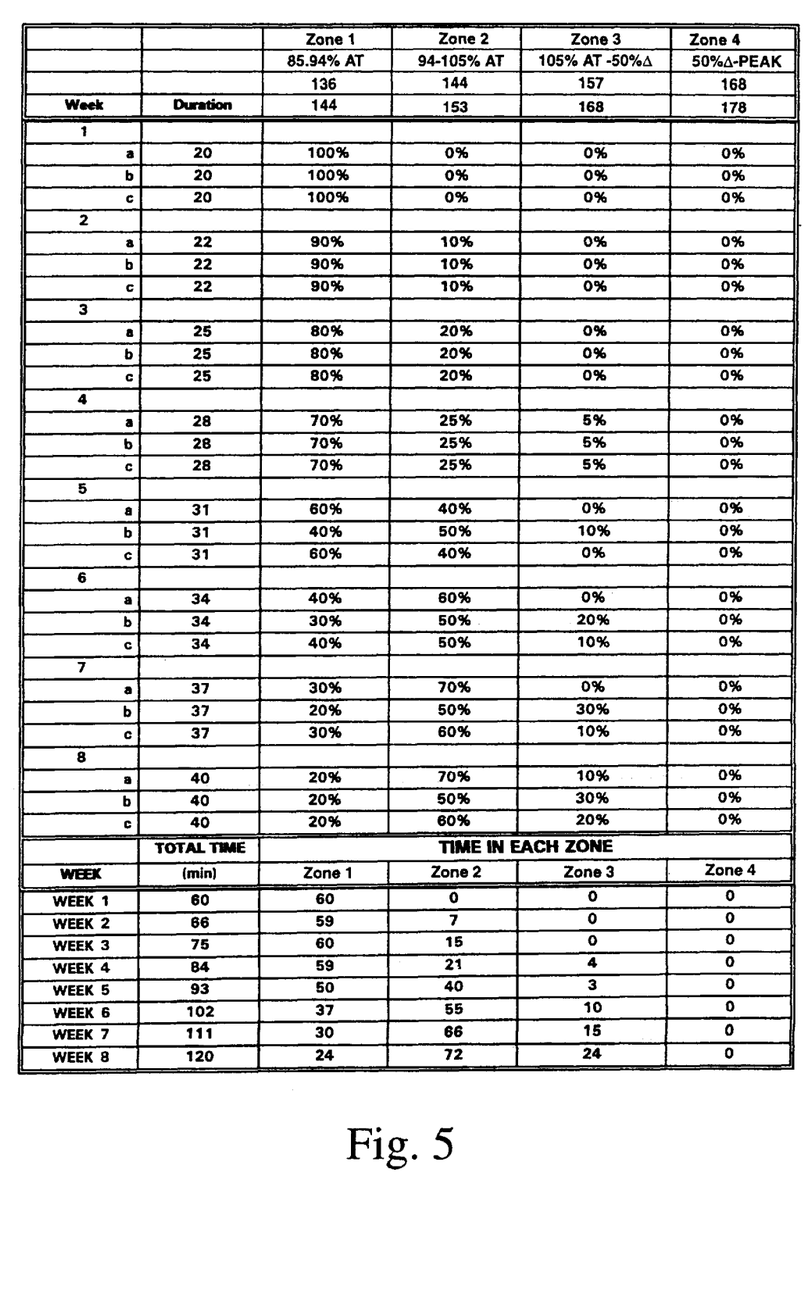
FIG. 5 schematically depicts a progressive eight-week exercise regimen consisting of a schedule of exercises to be performed at specified durations at specified intensities, the latter being a function of the individual's Anaerobic Threshold and $VO_2$max.
Figure 6:
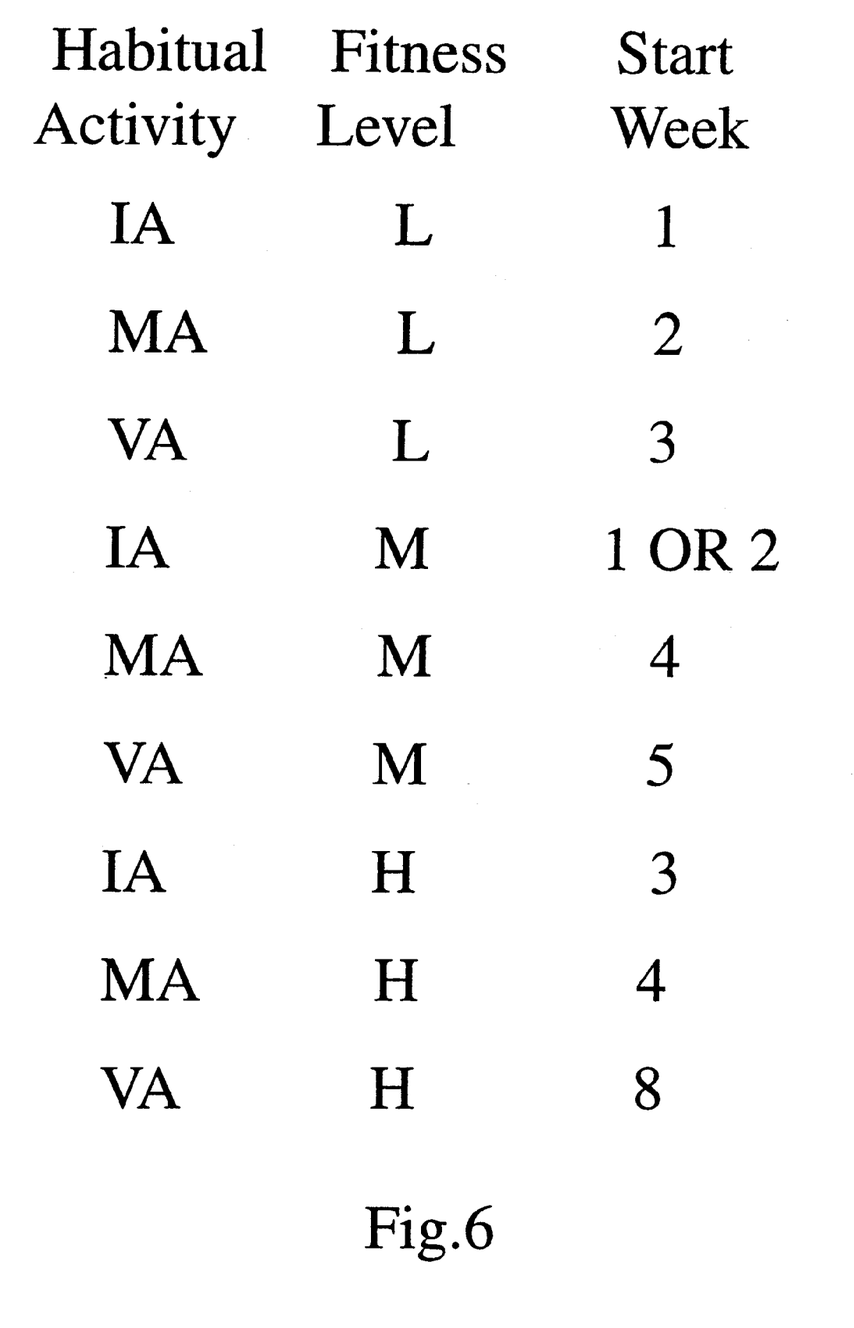
FIG. 6 comprises a chart depicting classifications for an individual's habitual activity level, namely, inactive (IA), moderately active (MA), or very active (VA), and fitness level, namely, low (L), medium (M), or high (H), utilized to determine the appropriate commencement level for the individual's particular exercise regimen as set forth in FIG. 5.

FIG. 5 further illustrates the progressive change in the partitioning of training intensities across the four zones as per the above example. This figure indicates that as training progresses week-by-week, time in higher intensity zones increases. However, the percentage of time in ZONE 3 is still relatively small for this untrained client, amounting to only 9% of the total training time.

Table 2 below summarizes the boundaries for the four heart rate zones used for training. Zone 1 is defined as 85% to 94% of the $VO_2$ at the Anaerobic Threshold. For example, if the physiologically defensible boundaries of exercise intensity acquired from an exercise test indicate an AT at a $VO_2$ of 1.6 L/min and a $VO_2$max of 3.1 L/min, Zone 1 would be limited by the heart rates corresponding to 85% (1.36 L/min) and 94% AT (1.50 L/min). Similarly, Zone 2 is delimited by the heart rates corresponding to 94% to 105% AT (1.50 L/min to 1.68 L/min). Zone 3 is delimited by the heart rates corresponding to 105% of the $VO_2$ at AT to the $VO_2$ at 50% Δ, (half the distance between $VO_2$ at AT and $VO_2$peak) or 1.68 L/min to 2.35 L/min. Zone 4 would consist of heart rates corresponding to $VO_2$ values of 2.35 L/min to $VO_2$peak or 3.1 L/min.

TABLE 2

HEART RATE TRAINING ZONES

|  | ZONE 1 | ZONE 2 | ZONE 3 | ZONE 4 |
|---|---|---|---|---|
| Athletes | RECOVERY 85–94% AT "Active Recovery" | ENDURANCE 94–105% AT "Aerobic Endurance" | TEMPO 105% AT-50%Δ* "High Intensity Strength" | $VO_2$ PEAK TRAINING 50%Δ*-$VO_2$peak "Interval Speed Workout" |
| Presently Inactive | START-UP 85–94% AT "Low Intensity" | ENDURANCE 94–105% AT "Aerobic Endurance" | TEMPO "High Intensity Strength" | $VO_2$ PEAK TRAINING "Interval Speed Workout" |
| Submax | Start-up 85–94% AT | Endurance 94–105% AT | Intervals 105% AT-peak |  |

*50%Δ represents 50% of the difference between the $VO_2$ at the Anaerobic Threshold and $VO_2$ peak.

By no means is the above program universal. It merely illustrates the heart zone concepts of variety in training intensity, careful progression, and objective determination of the training intensities. In this regard, special care should be taken to the extent training intensities or zones are implemented that elicit physical performance at or around an individual's $VO_2$max. As discussed above, such physical activity exacts a tremendous toll on the individual and, at present, it is believed that only the most well-conditioned athletes will be suitable for exercise regimens incorporating such zones or intensities.

On the other hand, it is contemplated that exercise regimens can be implemented for individuals who are sedentary and have moderate to poor cardiorespiratory conditioning. In this regard, it is believed that if so much as one physiological marker, namely, the Anaerobic Threshold, can be identified in such individuals and that moderate exercise regimens can be constructed focusing initially (and perhaps exclusively) on zones or training intensities that elicit an oxygen uptake or heart rate within the physiological domain falling at or below the Anaerobic Threshold (e.g., 50% to 100% of AT).

Accordingly, it is understood that the system and method described herein and shown in the drawings represents only a presently preferred embodiment of the present invention and that various modifications and additions may be made to such embodiment without departing from the spirit and scope of the invention.

What is claimed is:

1. A method for assessing the cardiorespiratory fitness of an individual and developing a cardiorespiratory conditioning exercise regimen based upon said assessment comprising the steps:

a) determining said individual's Anaerobic Threshold and corresponding heart rate thereat;

b) determining said individual's Respiratory Compensation Point and corresponding heart rate thereat; and c) scheduling a multiplicity of exercise activities wherein each one of said multiplicity of exercise activities includes a first training intensity which elicits from said individual a heart rate ranging from 70% of said individual's Anaerobic Threshold heart rate to 120% of said individual's Anaerobic Threshold heart rate and a second training intensity which elicits from said individual a heart rate ranging from 85% of said individual's Anaerobic Threshold heart rate to said individual's Respiratory Compensation Point heart rate.

2. The method of claim 1 wherein in step a), said Anaerobic Threshold is determined by measuring and comparing said individual's ventilatory equivalent for oxygen ($V_E/VO_2$) to said individual's ventilatory equivalent for carbon dioxide ($V_E/VCO_2$) and identifying when said ventilatory equivalent for oxygen increases relative to said ventilatory equivalent for carbon dioxide as said individual engages in a monitored exercise activity.

3. The method of claim 1 wherein in step a), said Anaerobic Threshold is determined by measuring and comparing said individual's $CO_2$ output and oxygen uptake and identifying when said $CO_2$ output increases disproportionately to said $O_2$ uptake as said individual engages in a monitored exercise activity.

4. A method for assessing the cardiorespiratory fitness of an individual and developing a cardiorespiratory conditioning exercise regimen based upon said assessment comprising the steps:

a) determining said individual's Anaerobic Threshold and corresponding heart rate thereat; and b) scheduling a multiplicity of exercise activities wherein each respective one of said multiplicity of exercise activities elicits a heart rate in said individual ranging between 70% to 120% of the individual's corresponding Anaerobic Threshold heart rate.

5. The method of claim 4, wherein in step b), each one of said multiplicity of said exercise activities elicits a heart rate in said individual ranging between 70% to 110% of said individual's corresponding Anaerobic Threshold heart rate.

6. A method for assessing the cardiorespiratory fitness of an individual and developing a cardiorespiratory conditioning exercise regimen based upon said assessment comprising the steps:

a) determining said individual's Anaerobic Threshold and corresponding heart rate thereat;

b) determining said individual's Respiratory Compensation Point and corresponding heart rate thereat;

c) determining the individual's VO2max and corresponding heart rate thereat; and d) scheduling a multiplicity of exercise activities wherein each respective one of said multiplicity of exercise activities elicits a heart rate in said individual ranging between 70% of the individual's corresponding Anaerobic Threshold heart rate and the individual's $VO_2$max heart rate.

7. The method of claim 6, wherein in step c), each one of said multiplicity of said exercise activities includes a first training intensity which elicits from said individual a heart rate ranging from 70% of said individual's corresponding Anaerobic Threshold heart rate to said individual's RCP heart rate, and a second training intensity which elicits from said individual a heart rate ranging from 85% of said individual's Anaerobic Threshold heart rate to said individual's VO2 max heart rate.

8. The method of claim 6, wherein in step c), each one of said multiplicity of said exercise activities includes a first training intensity which elicits from said individual a heart rate ranging from 70% to 105% of said individual's corresponding Anaerobic Threshold heart rate, a second training intensity which elicits from said individual a heart rate ranging from 85% of said individual's Anaerobic Threshold heart rate to 50% of said individual's RCP heart rate, a third training intensity which elicits from said individual a heart rate ranging from 95% of said individual's Anaerobic Threshold heart rate to 50% of said individual's VO2 max heart rate, and a fourth training intensity which elicits from said individual a heart rate ranging from 100% of said individual's Anaerobic Threshold heart rate to said individual's VO2 max heart rate.

9. A method for assessing the cardiorespiratory fitness of an individual and developing a cardiorespiratory conditioning exercise regiment based upon said assessment comprising the steps:
   a) determining said individual's Anaerobic Threshold and corresponding heart rate thereat;
   b) determining said individual's Respiratory Compensation Point and corresponding heart rate thereat; and
   c) scheduling a multiplicity of exercise activities wherein each one of said multiplicity of exercise activities includes a first training intensity which elicits from said individual a heart rate ranging from 70% of said individual's Anaerobic Threshold heart rate to 110% of said individual's Anaerobic Threshold heart rate, a second training intensity being designed to elicit from said individual a heart rate ranging from 85% of said individual's Anaerobic Threshold heart rate to 50% of said individual's Respiratory Compensation Point heart rate, and a third training intensity being designed to elicit from said individual a heart rate ranging from 90% of said individual's Anaerobic Threshold heart rate to said individual's Respiratory Compensation Point heart rate.

10. A method for assessing the cardiorespiratory fitness of an individual and developing a cardiorespiratory conditioning exercise regiment based upon said assessment comprising the steps:
   a) determining said individual's Anaerobic Threshold and corresponding heart rate thereat;
   b) determining said individual's Respiratory Compensation Point and corresponding heart rate thereat; and
   c) scheduling a multiplicity of exercise activities wherein each one of said multiplicity of exercise activities includes a first training intensity which elicits from said individual a heart rate ranging from 70% of said individual's Anaerobic Threshold heart rate to 105% of said individual's Anaerobic Threshold heart rate, a second training intensity being designed to elicit from said individual a heart rate ranging from 90% of said individual's Anaerobic Threshold heart rate to 120% of said individual's Anaerobic Threshold heart rate, a third training intensity being designed to elicit from said individual a heart rate ranging from 95% of said individual's Anaerobic Threshold heart rate to 75% of said individual's Respiratory Compensation Point heart rate, and a fourth training intensity being designed to elicit from said individual a heart rate ranging from 100% of said individual's Anaerobic Threshold heart rate to said individual's Respiratory Compensation Point heart rate.

* * * * *